United States Patent [19]

VandenBerg

[11] Patent Number: Plant 6,772

[45] Date of Patent: May 2, 1989

[54] CHRYSANTHEMUM PLANT NAMED PICO

[75] Inventor: Cornelis P. VandenBerg, Salinas, Calif.

[73] Assignee: Yoder Brothers, Inc., Barberton, Ohio

[21] Appl. No.: 135,294

[22] Filed: Dec. 21, 1987

[51] Int. Cl.[4] ..... A01H 5/00
[52] U.S. Cl. ..... Plt./74
[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Pico particularly characterized by its flat capitulum form; spoon daisy capitulum type; yellow ray floret color; diameter across face of capitulum of up to 13 cm at maturity when grown as a pinched disbudded pot mum; uniform eight week photoperiodic flowering response to short days; medium plant height when grown as a pinched pot mum; recommended as disbudded pot mum; spreading and prolific branching pattern.

3 Drawing Sheets

The present invention comprises a new and distinct cultivar of Chrysanthemum, botanically known as *Chrysanthemum morifolium,* Ramat., and referred to by the cultivar name Pico.

Pico, identified as 82208013, was originated from a cross made by Cornelis P. VandenBerg in a controlled breeding program in Salinas, Calif. in 1982.

The female parent of Pico was an unnamed seedling identified as 77423014. The male parent of Pico was an unnamed seedling identified as 80032001.

Pico was discovered and selected as one flowering plant within the progeny of the stated cross by Cornelis P. VandenBerg in December of 1982, in a controlled environment in Salinas, Calif.

The first act of asexual reproduction of Pico was accomplished when vegetative cuttings were taken from the initial selection in March of 1983 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Pico are firmly fixed and are retained through successive generations of asexual reproduction.

Pico has not been observed under all possible environmental conditions. The phenotype may vary significantly with variations in environment such as temperature, light intensity, and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Pico, which, in combination, distinguish this Chrysanthemum as a new and distinct cultivar:

1. Flat capitulum form.
2. Spoon daisy capitulum type.
3. Yellow ray floret color.
4. Diameter across face of capitulum up to 13 cm at maturity when grown as a pinched disbudded pot mum.

5. Uniform eight week photoperiodic flowering response to short days.
6. Medium plant height, requiring 0 to 7 long days after pinch prior to short days and 1 application of 2500 ppm B-9 SP to attain a flowered plant height of 25 to 35 cm for year-round flowerings when grown as a pinched pot mum.
7. Recommended as disbudded pot mum.
8. Spreading and prolific branching pattern.

The accompanying photographic drawings show typical inflorescence and leaf characteristics of Pico, with the colors being as nearly true as possible with illustrations of this type.

Sheet 1 is a color photograph of Pico grown as a pinched disbudded pot mum.

Sheet 2 is a black and white photograph of three views of the inflorescence of Pico.

Sheet 3 is a black and white photograph showing the upper and under sides of the leaves of Pico at three stages of development (mature, intermediate and immature).

Of the commercial cultivars known to the inventor, the most similar in comparison to Pico is Neoga, disclosed in applicant's pending Plant patent application Ser. No. 920,270. Reference is made to attached Chart A, which compares certain characteristics of Pico to the same characteristics of Neoga.

Similar traits are capitulum form and type, branching pattern, plant height and flowering response. Pico has a yellow ray floret color, whereas Neoga has a purple ray floret color. Also, the branching pattern of Pico is more prolific than Neoga, and Pico has a larger capitulum diameter than Neoga.

In the following description, color references are made to The Royal Horticultural Society Colour Chart. The color values were determined on plant material grown as a pinched disbudded pot mum in Salinas, Calif. on June 11, 1987.

Classification:

*Botanical.*—*Chrysanthemum morifolium,* Ramat., cv. Pico.

*Commercial.*—Spoon daisy disbud and spray pot mum.

INFLORESCENCE

A. Capitulum:

*Form.*—Flat.

*Type.*—Spoon daisy.

*Diameter across face.*—Up to 13 cm at maturity.

B. Corolla of ray florets:

*Color (general tonality from a distance of three meters).*—Yellow.

*Color (upper surface) (spoon tips).*—3A.

*Color (under surface) (tubes).*—3A.

*Shape.*—Base tubular. Distal portion open, flattened and spoon like. Spoon length is varying, ranging from 30% to 70% of the length of the ray floret, with an average of approximately 50%. At maturity the spoon tips twist.

C. Corolla of disc florets:

*Color (mature).*—Closest to 9A.

*Color (immature).*—Closest to 144A to 144B.

D. Reproductive organs:

*Androecium.*—Present on disc florets only; no pollen.

*Gynoecium.*—Present on both ray and disc florets.

PLANT

A. General appearance:

*Height.*—Medium; 25 to 35 cm as a pinched pot mum with 0 to 7 long days after pinch prior to short days and 1 application of 2500 ppm B-9 SP.

*Branching pattern.*—Spreading and prolific.

B. Foliage:

*Color (upper surface).*—137A to 147A.

*Color (under surface).*—147B.

*Shape.*—Lobed and very slightly serrated.

CHART A

Comparison of Pico and Neoga

| Cultivar | Ray Floret Color | Capitulum Form and Type | Branching Pattern |
|---|---|---|---|
| Pico | Yellow | Spoon daisy | Spreading and prolific |
| Neoga | Purple | Spoon daisy | Spreading |

| Cultivar | Diameter across face of capitulum | Plant height | Flowering response period |
|---|---|---|---|
| Pico | Up to 13 cm | Medium | 8 weeks |
| Neoga | Up to 12 cm | Medium | 8 weeks |

Comparisons made of pinched disbudded pot mums grown in Salinas, California

I claim:

1. A new and distinct Chrysanthemum plant named Pico, as described and illustrated, and parts thereof.

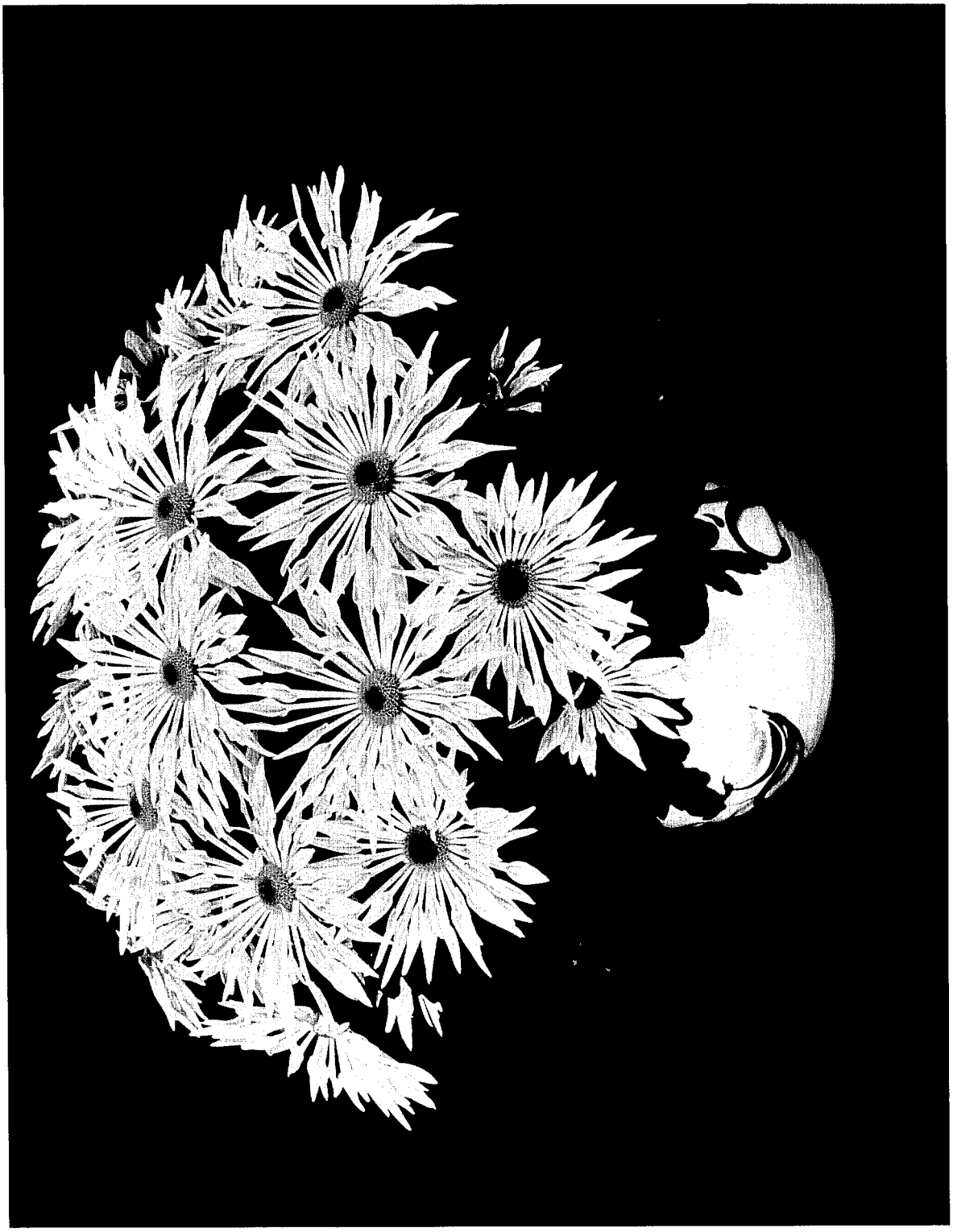

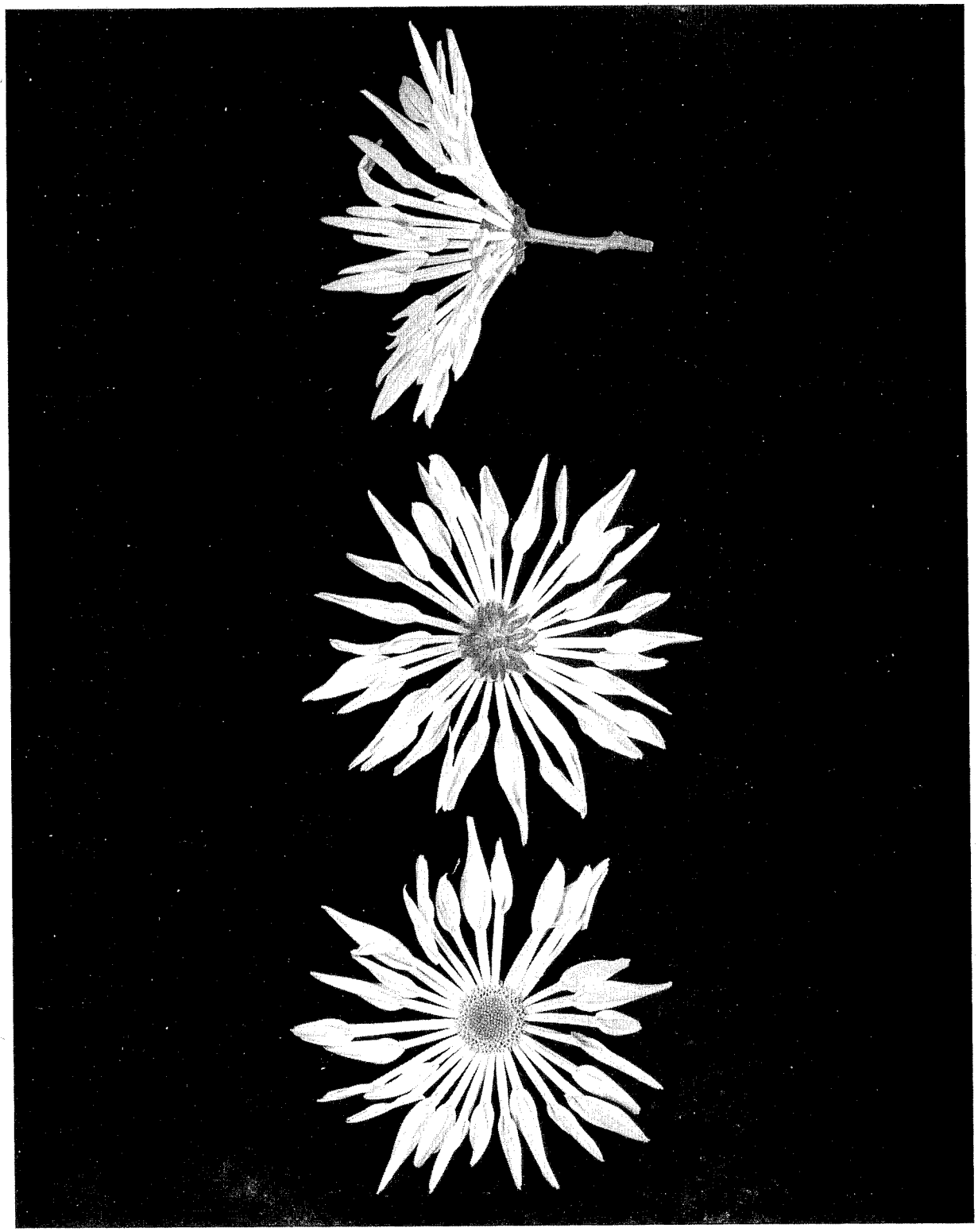

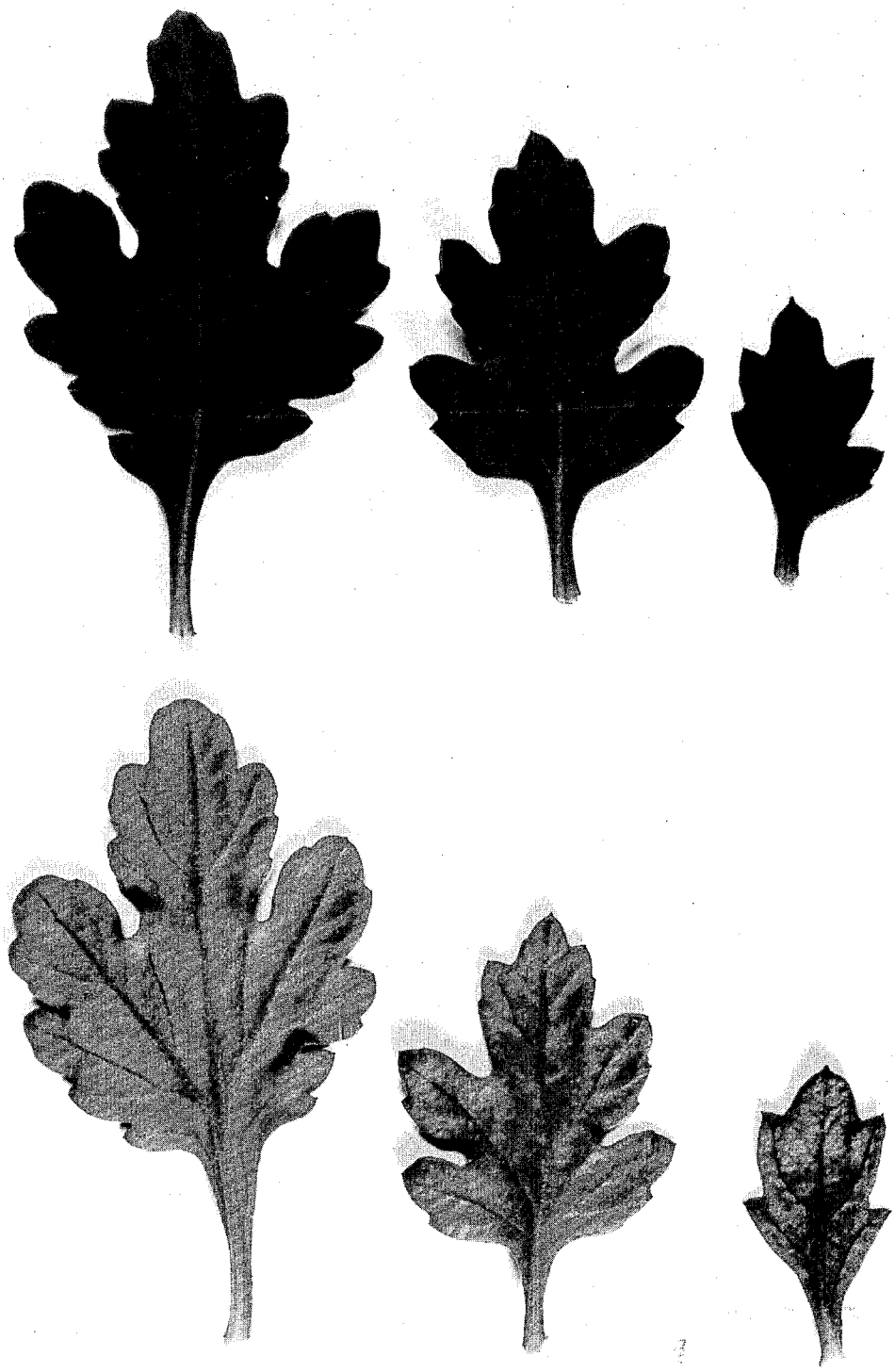

* * * * *